US012429484B2

(12) United States Patent
Stowe et al.

(10) Patent No.: US 12,429,484 B2
(45) Date of Patent: Sep. 30, 2025

(54) HOMOGENEOUS ENZYME IMMUNOASSAY FOR KERATINIZED STRUCTURES

(71) Applicant: Psychemedics Corporation, Acton, MA (US)

(72) Inventors: Gary Neil Stowe, Manhattan Beach, CA (US); Elvan Loni, Torrance, CA (US); Virginia Ann Hill, Los Angeles, CA (US); Michael Irving Schaffer, Los Angeles, CA (US)

(73) Assignee: Psychemedics Corporation, Acton, MA (US)

( * ) Notice: Subject to any disclaimer, the term of this patent is extended or adjusted under 35 U.S.C. 154(b) by 905 days.

(21) Appl. No.: 17/507,167

(22) Filed: Oct. 21, 2021

(65) Prior Publication Data

US 2022/0120748 A1 Apr. 21, 2022

Related U.S. Application Data

(63) Continuation of application No. 16/570,667, filed on Sep. 13, 2019, now abandoned.

(60) Provisional application No. 62/889,870, filed on Aug. 21, 2019, provisional application No. 62/887,191, filed on Aug. 15, 2019.

(51) Int. Cl.
*G01N 33/573* (2006.01)
*G01N 33/94* (2006.01)

(52) U.S. Cl.
CPC .... *G01N 33/573* (2013.01); *C12Y 101/01049* (2013.01); *G01N 33/946* (2013.01); *G01N 33/9486* (2013.01); *G01N 2430/00* (2013.01)

(58) Field of Classification Search
CPC ............... G01N 33/573; G01N 33/946; G01N 33/9486; G01N 2430/00; G01N 2333/904; G01N 33/94; C12Y 101/01049
See application file for complete search history.

(56) References Cited

U.S. PATENT DOCUMENTS

| | | | |
|---|---|---|---|
| 3,817,837 A | 6/1974 | Rubenstein | |
| 4,275,149 A | 6/1981 | Litman | |
| 4,318,980 A | 3/1982 | Boguslaski | |
| 4,686,181 A | 8/1987 | Doná | |
| 4,956,778 A | 9/1990 | Naito | |
| 5,091,513 A | 2/1992 | Huston | |
| 5,132,405 A | 7/1992 | Huston | |
| 5,733,743 A | 3/1998 | Johnson | |
| 6,033,890 A | 3/2000 | Jakobovits | |
| 6,582,924 B1 | 6/2003 | Werner | |
| 8,084,215 B2 * | 12/2011 | Hill | G01N 33/9486 435/7.1 |
| 2006/0046273 A1 | 3/2006 | Lin | |
| 2009/0155929 A1 | 6/2009 | Wei et al. | |
| 2016/0312208 A1 | 10/2016 | Zheng | |
| 2021/0048436 A1 | 2/2021 | Stowe et al. | |

FOREIGN PATENT DOCUMENTS

EP 2742352 B1 2/2018
WO WO 2015/094852 6/2015

OTHER PUBLICATIONS

Hill, V. et al. Multiple Aspects of Hair Analysis for Opiates: Methodology, Clinical and Workplace Populations, Codeine and Poppy Seed Ingestion, 2005, Journal of Analytical Technology, 29: 696-703 (Year: 2005).*
Adams et al., "Crystallization and Preliminary X-ray Data for Glucose-6-phosphate Dehydrogenase from Leuconostoc mesentemides", J. Biol. Chem., vol. 258:9, 5867-5868, 1983.
Barnell et al., "Sequence and Genetic Organization of a Zymomonas mobilis Gene Cluster That Encodes Several Enzymes of Glucose Metabolism", J. Bacterial., vol. 172: 12, 7227-7240, 1990.
Bhadbade et al., "Sequence identity between a lysine-containing peptide from Leuconostoc mesenteroides glucose-6-phosphate dehydrogenase and an active site peptide from human erythrocyte glucose-6-phosphate dehydrogenase.", FEES Lett. vol. 211, 243-246, 1987.
Heilmann et al., "Identification and isolation of glucose dehydrogenase genes of Bacillus megaterium M1286 and their expression in *Escherichia coli.*", Eur. J. Biochem. vol. 174, 485-490, 1988.
Huston et al., "Protein engineering of antibody binding sites: Recovery of specific activity in an anti-digoxin single-chain Fv analogue produced in *Escherichia coli*", Proc. Natl. Acad. Sci. USA, 85: 5879-5883, 1988.
International Preliminary Report on Patentability in Appln. No. PCT/US2020/046459, dated Feb. 8, 2022, 8 pages.
Jeffrey et al., "Glucose 6-phosphate dehydrogenase from *Saccharomyces cerevisiae*: characterization of a reactive lysine residue labeled with acid", Biochemistry, vol. 24, 666-671, 1985.
Jeffrey et al., "Glucose-6-phosphate dehydrogenase. Characterization of a reactive lysine residue in the Pichia jadinii enzyme reveals a limited structural variation in a functionally significant segment.", Biochem. Biopys. Res. Comm., vol. 160: 3, 1290-1295, 1989.
Lee et al., "Cloning of the Gene and Amino Acid Sequence for Glucose 6- Phosphate Dehydrogenase from Leuconostoc mesenteroides", J. Biol. Chem., vol. 266: 20, 13028-13034, 1991.
Levy, "Glucose-6-phosphate dehydrogenases.", Adv. Enzym. vol. 48, 97-192, 1979.
Murphy et al., "Expression of the Gene for NAD-Dependent Glucose-6-Phosphate Dehydrogenase from Leuconostoc mesenteroides Cloned in *Escherichia coli* K-12", J. Bacterial., vol. 169: 1, 334-339, 1987.

(Continued)

*Primary Examiner* — Louise W Humphrey
*Assistant Examiner* — Alexander M Duryee
(74) *Attorney, Agent, or Firm* — Fish & Richardson P.C.

(57) ABSTRACT

Methods and kits for determining the presence and/or amount of one or more analytes in a keratinized structure (e.g., hair) sample. Such methods can include combining in an aqueous medium: a conjugate comprising an enzyme and an analyte of interest, an antibody specific for the analyte of interest, and the keratinized structure sample, and then determining whether the analyte of interest is present or absent in the keratinized structure sample.

20 Claims, 3 Drawing Sheets

(56) References Cited

OTHER PUBLICATIONS

PCT International Search Report and Written Opinion in International Appln. No. PCT/US2020/046459, dated Nov. 20, 2020, 13 pages.
Reiter et al., "Disulfide stabilization of antibody Fv: computer predictions and experimental evaluation.", Protein Eng., vol. 8, 1323-1331, 1995.
Rowley et al., "Molecular Characterization of the *Escherichia coli* K-12 zwf Gene Encoding Glucose 6-Phosphate Dehydrogenase", J. Bacterial., vol. 173: 3, 968-977, 1991.
SAMHSA Proposed Guidelines vol. 69, No. 71, p. 19673-19732, 2004.
SAMHSA Proposed Guidelines vol. 80, No. 94, p. 28054-28101, 2015.
Felgate, "Methods of Analysis-Initial Testing," Encyclopedia of Forensic Sciences, Feb. 2013, pp. 249-264.
Law et al., "The Evaluation of an Homogeneous Enzyme Immunoassay (Emit) and Radioimmunoassay for Barbiturates," Journal of the Forensic Science Society, Jan. 1, 1981, 21(1):55-66.
Skrzipczyk et al., "Bioanalytical Assays: RIA/EIA," Drug Discovery and Evaluation: Safety and Pharmacokinetic Assays, Mar. 2013, pp. 869-885.

\* cited by examiner

HOMOGENEOUS ENZYME IMMUNOASSAY FOR KERATINIZED STRUCTURES

CROSS-REFERENCE TO RELATED APPLICATIONS

This application is a continuation of U.S. application Ser. No. 16/570,667, filed Sep. 13, 2019, which claims priority to U.S. Provisional Application Ser. No. 62/889,870, filed on Aug. 21, 2019, and 62/887,191, filed Aug. 15, 2019, the contents of which are hereby incorporated by reference in their entireties.

TECHNICAL FIELD

This disclosure relates to methods and kits for determining the presence and/or amount of one or more analytes in a keratinized structure (e.g., hair) sample and more particularly to methods and kits for doing the same using competitive immunoassays.

BACKGROUND

Immunoassays such as radioimmunoassays (RIA) and homogeneous enzyme immunoassays (HEIA) are useful methods for determining the presence, identity, and amount of one or more analytes of interest in a sample. In particular, the measurement of trace amounts of analytes, particularly chemical substances, has become essential for many health care applications in pharmaceutical studies, therapeutic drug monitoring, and for drug abuse detection. Often, a sample, particularly a sample of a keratinized structure (e.g., hair) or a biological fluid (e.g., oral fluid, blood, urine) obtained from an individual, is screened for the presence of one or more analytes (e.g., illicit and non-illicit drugs).

The present disclosure relates to methods and assay that overcome the current obstacles and limitations and provides homogeneous enzyme immunoassay methods and kits for the qualitative determination of low concentration analytes in keratinized structure (e.g., hair) samples.

SUMMARY

Provided herein is a method for determining the presence or absence of an analyte of interest in a keratinized structure sample comprising: combining in an aqueous medium: a conjugate comprising an enzyme and the analyte of interest; an antibody specific for the analyte of interest; and the keratinized structure sample; and determining if the analyte of interest is present or absent in the keratinized structure sample.

In some embodiments, the enzyme is selected from the group consisting of glucose-6-phosphate dehydrogenase (G6PDH), alcohol dehydrogenase, glutamic dehydrogenase, malic dehydrogenase, isocitric dehydrogenase, α-glycerol phosphate dehydrogenase, lactic dehydrogenase, glyceraldehydes-3-phosphate dehydrogenase, gluthathione reductase, quinine reductase, nitrate reductase, and glutamic dehydrogenase. In some embodiments, the enzyme is glucose-6-phosphate dehydrogenase (G6PDH). In some embodiments, the G6PDH is covalently linked to the analyte of interest.

In some embodiments, the antibody specific for the analyte of interest is selected from the group consisting of cocaine, benzoylecgonine, cocaethylene, norcocaine, PCP, amphetamine, methamphetamine, cannabinoids, THC, carboxy-THC, heroin, benzodiazepines, methadone, codeine, morphine, 6-monoacetylmorphine (MAM), oxycodone, 3,4-methylenedioxyamphetamine (MDA), and 3,4-methylenedioxymethamphetamine (MDMA). In some embodiments, the antibody is detectably labeled.

In some embodiments, the G6PDH is obtained from a natural source. In some embodiments, the G6PDH is a recombinant enzyme.

In some embodiments, the aqueous medium further comprises: an enzyme substrate for G6PDH; and a coenzyme for G6PDH. In some embodiments, the method further comprises detecting a change in the enzymatic activity of the enzyme-analyte conjugate, wherein the change in enzymatic activity is related to the amount of the analyte of interest present in the sample.

In some embodiments, the antibody is present at a concentration from about 0.4 µg/mL to about 1.0 µg/mL. In some embodiments, the conjugate comprising an enzyme and the analyte of interest is present at a concentration from about 0.4 µg/mL to about 0.5 µg/mL.

In some embodiments, the determining the presence or absence of the analyte of interest is determined at a temperature of about 4° C. to about 45° C. In some embodiments, the determining the presence or absence of the analyte of interest is determined at a temperature of about 30° C. to about 40° C. In some embodiments, the determining the presence or absence of the analyte of interest is determined at a temperature of about 37° C.

In some embodiments, the aqueous medium has a pH range of about 4.0 to about 11.0. In some embodiments, the aqueous medium has a pH of about 7.0. In some embodiments, the aqueous medium contains less than about 20% of a polar solvent. In some embodiments, the aqueous medium contains less than about 20% of N,N-Dimethylformamide (DMF), acetonitrile, dimethylsulfoxide (DMSO), methanol, or a combination thereof.

In some embodiments, the analyte of interest is selected from the group consisting of a drug of abuse, a toxic chemical, an environmental chemical, a petroleum product, a natural product, an organic compound, a nutrient, a prescription and over-the-counter medication, or a metabolite, derivative, or breakdown product of any of the foregoing. In some embodiments, the analyte of interest is a drug of abuse or metabolite thereof. In some embodiments, the drug of abuse or metabolite thereof is selected from the group consisting of cocaine, benzoylecgonine, cocaethylene, norocaine, PCP, amphetamine, methamphetamines, cannabinoids, THC, carboxy-THC, nicotine, cotinine, benzodiazepines, heroin, codeine, morphine, 6-monoacetylmorphine (MAM), oxycodone, 3,4-methylenedioxyamphetamine (MDA), and 3,4-methylenedioxymethamphetamine (MDMA). In some embodiments, the analyte of interest is selected from the group consisting of opioids, amphetamines, NSAIDS, steroids, cannabinoids, benzodiazepines, barbiturates, tricyclics, nicotine, and ephedrines, or metabolites, derivatives, or breakdown products of any of the foregoing.

Also provided herein is a method for determining the presence or absence of an analyte of interest in a keratinized structure sample comprising: combining in an aqueous medium: an enzyme-analyte conjugate comprising glucose-6-phosphate dehydrogenase (G6PDH) covalently linked to the analyte of interest; an antibody specific for the analyte of interest; a keratinized structure sample; an enzyme substrate for G6PDH; and a coenzyme for G6PDH; and determining if the analyte of interest is present or absent in the keratinized structure sample.

Also provided herein is a method for determining the presence or absence of an analyte of interest in a keratinized structure sample comprising: combining in an aqueous medium: an enzyme-analyte conjugate comprising glucose-6-phosphate dehydrogenase (G6PDH) covalently linked to the analyte of interest; an antibody specific for the analyte of interest; a keratinized structure sample; an enzyme substrate for G6PDH; and a coenzyme for G6PDH; and determining if the analyte of interest is present or absent in the keratinized structure sample, wherein the analyte of interest is a drug of abuse or metabolite thereof.

In some embodiments, the keratinized structure sample is a hair sample. In some embodiments, the keratinized structure sample is a nail sample.

Also provided herein is a kit comprising: a conjugate comprising an enzyme and an analyte of interest; and an antibody specific for the analyte of interest.

In some embodiments, the enzyme is selected from the group consisting of glucose-6-phosphate dehydrogenase (G6PDH), alcohol dehydrogenase, glutamic dehydrogenase, malic dehydrogenase, isocitric dehydrogenase, α-glycerol phosphate dehydrogenase, lactic dehydrogenase, glyceraldehydes-3-phosphate dehydrogenase, gluthathione reductase, quinine reductase, nitrate reductase, and glutamic dehydrogenase. In some embodiments, the enzyme is glucose-6-phosphate dehydrogenase (G6PDH). In some embodiments, the enzyme is glucose-6-phosphate dehydrogenase (G6PDH).

In some embodiments, the antibody specific for the analyte of interest is selected from the group consisting of cocaine, benzoylecgonine, cocaethylene, norcocaine, PCP, amphetamine, methamphetamine, cannabinoids, THC, carboxy-THC, heroin, benzodiazepines, methadone, codeine, morphine, 6-monoacetylmorphine (MAM), oxycodone, 3,4-methylenedioxyamphetamine (MDA), and 3,4-methylenedioxymethamphetamine (MDMA).

In some embodiments, the G6PDH is obtained from a natural source. In some embodiments, the G6PDH is a recombinant enzyme.

In some embodiments, the kit further comprises: an enzyme substrate for G6PDH; and a coenzyme for G6PDH.

In some embodiments, the analyte of interest is selected from the group consisting of a drug of abuse, a toxic chemical, an environmental chemical, a petroleum product, a natural product, an organic compound, a nutrient, a prescription, and over-the-counter medication, or a metabolite, derivative, or breakdown product of any of the foregoing. In some embodiments, the analyte of interest is a drug of abuse or metabolite thereof. In some embodiments, the drug of abuse or metabolite thereof is selected from the group consisting of cocaine, benzoylecgonine, cocaethylene, norocaine, PCP, amphetamine, methamphetamines, cannabinoids, THC, carboxy-THC, nicotine, cotinine, benzodiazepines, heroin, codeine, morphine, 6-monoacetylmorphine (MAM), oxycodone, 3,4-methylenedioxyamphetamine (MDA), and 3,4-methylenedioxymethamphetamine (MDMA).

In some embodiments, the analyte of interest is selected from the group consisting of opioids, amphetamines, NSAIDS, steroids, cannabinoids, benzodiazepines, barbiturates, tricyclics, nicotine and ephedrines, or metabolites, derivatives, or breakdown products of any of the foregoing.

All publications, patents, and patent applications mentioned in this specification are herein incorporated by reference to the same extent as if each individual publication, patent, or patent application was specifically and individually indicated to be incorporated by reference. To the extent publications and patents or patent applications incorporated by reference contradict the disclosure contained in the specification, the specification is intended to supersede and/or take precedence over any such contradictory material.

Other features and advantages of the methods as provided herein will be apparent from the following detailed description and figures, and from the claims.

DETAILED DESCRIPTION

Figure 1:
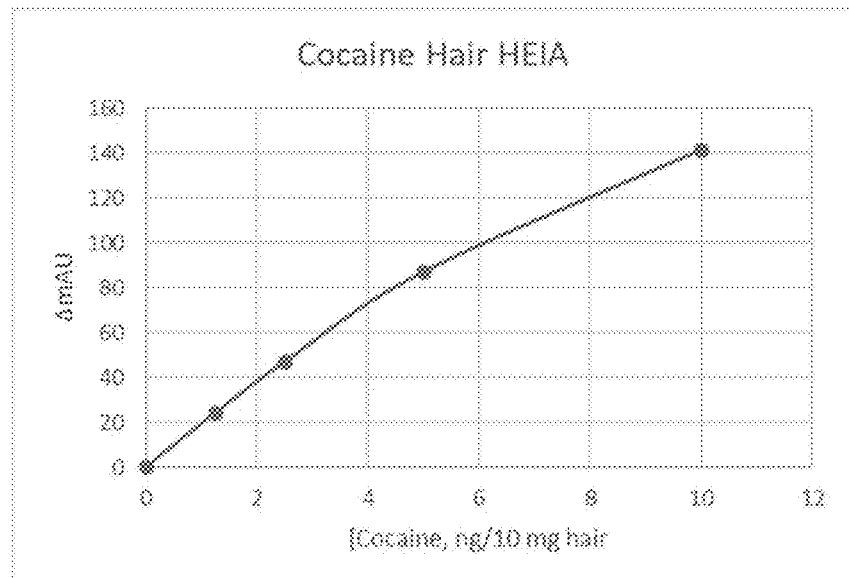
FIG. 1 is an exemplary graphical representation of a calibration curve for cocaine obtained by plotting the results obtained in Example 6. The concentration of cocaine is shown on the X-axis and the absorbance at 340 nm (ΔmAU) is shown on the Y-axis.

The present disclosure relates to methods and kits for a homogeneous enzyme immunoassay for the qualitative determination of analytes (e.g., low concentration analytes) in keratinized structure (e.g., hair) samples.

Current methods used to screen for particular analytes are regulated by the Substance Abuse mental Health Services Administration (SAMHSA). These regulations include cut-off calibrator concentrations for approved screening assays and these cutoffs vary depending on the sample used for screening as well as the analyte being detected. As shown in Table A, the calibrator concentrations for many typical analytes detected in hair are 1.5- to 10-fold lower than those for oral fluid.

TABLE A

| Test Analyte | Oral Fluid Calibrator (ng/mL)[1] | Test Analyte | Hair Calibrator (ng/10 mg)[2] |
|---|---|---|---|
| Cocaine | 15 | Cocaine | 5 |
| Opioids | 30 | Opioids | 2 |
| 6-Acetylmorphine | 3 | 6-Acetylmorphine | 2 |
| Phencyclidine | 3 | Phencyclidine | 3 |
| Amphetamines | 25 | Amphetamines[3] | 3 |

[1]SAMHSA Proposed Guidelines Vol. 80, No. 94, p. 28054-28101, 2015
[2]SAMHSA Proposed Guidelines Vol. 69, No. 71, p. 19673-19732
[3]510(k) k051161

This significant decrease in calibrator concentrations for hair samples as compared to oral fluid samples represents a challenge for developing a homogeneous enzyme immunoassay for hair. In addition, the hair matrix presents potential confounding substances (e.g., cosmetic treatments, hair styling products, hair care products, deodorants) that can be extracted during extraction of the analyte of interest from the hair. These same confounding substances are not found in oral matrices. For example, keratinized structures such as hair maintain potentially confounding substances throughout the length of the segment tested, this is not, however, the case for liquid matrices (e.g., urine and oral fluid) where the interfering substances only include those present during the short time period before and during sample collection. Finally, the hair matrix is a solid matrix with very minimal analyte concentrations present and the amount of solid hair matrix employed is limited by the amount of extraction solution. Meaning, more hair cannot always be added to the extraction solution, thus limiting the concentration of the drug that can be eluted.

Overall, these limitations make the final sample to use in the homogeneous immunoassay not only extremely low in abundance but also low in purity, posing significant obstacles to overcome while developing a homogeneous immunoassay for hair exhibiting the required sensitivity and specificity.

Provided herein is a method for determining the presence or absence of an analyte of interest in a keratinized structure (e.g., hair) sample, comprising first combining in an aqueous medium: a conjugate comprising an enzyme and the analyte of interest, an antibody specific for the analyte of interest, and the keratinized structure (e.g., hair) sample, and then determining whether the analyte of interest is present or absent in the keratinized structure (e.g., hair) sample.

Enzymes, Coenzymes, and Substrates

The methods provided herein use, as one component, a conjugate comprising an enzyme and the analyte of interest.

In some embodiments, the enzyme utilizes nicotinamide adenine dinucleotide (NAD/NAD+) or nicotinamide adenine dinucleotide phosphate (NADP/NADP+) as a co-enzyme to generate NADH and NADPH, respectively. For example, the enzyme can be glucose-6-phosphate dehydrogenase (G6PDH). In some embodiments, the enzyme is an enzyme other G6PDH. Non-limiting examples of additional enzymes that are useful for the present disclosure and which use NAD (NAD+) as a co-enzyme and generate NADH include, alcohol dehydrogenase, glutamic dehydrogenase, malic dehydrogenase, isocitric dehydrogenase, α-glycerol phosphate dehydrogenase, lactic dehydrogenase, and glyceraldehydes-3-phosphate dehydrogenase. Non-limiting examples of additional enzymes that are useful for the methods described herein and which use NADP (NADP+) as a co-enzyme and generate NADPH include gluthathione reductase, quinine reductase, nitrate reductase, and glutamic dehydrogenase. Further non-limiting examples of enzymes and co-enzymes useful in the methods provided herein are disclosed in U.S. Pat. Nos. 4,275,149 and 4,318,980, which are each incorporated herein by reference in their entirety.

In some embodiments, the G6PDH is capable of using both NADP+ and NAD+. For example, those isolated from *Leuconostoc mesenteroides, A. suboxydans, P. aeruginosa, Pseudomonas* W6, H. eutrophaH-16, Hydrogenomonas facilis, *Arthrobacter* 7C, *A. beijerinckii, T. ferrooxidans, B. licheniformis, P. denitrificans, C. crescentus, L. lactis,* and *R. spheroides*. In some embodiments, G6PDH is capable of using NAD+ as a preferred cofactor. For example, those isolated from *P. fluorescens* and one of the G6PDHs from *P. multivorans*. In some embodiments, the G6PDH is NAD+ specific. For example, one of the G6PDHs from *A. xylinum*. As another example, *Leuconostoc mesenteroides* glucose-6-phosphate dehydrogenases are dimeric enzymes that have the ability to catalyze the oxidation of D-glucose-6-phosphate to D-glucono-δ-lactone-6-phosphate by utilizing either NAD+ or NADP+. This property of using NAD+ differentiates these enzymes from human G6PDH, which utilizes only NADP+ effectively, and allows *L. mesenteroides*-specific G6PDH activity to be measured in the presence of human G6PDH, as, for example, in human samples.

In some embodiments, the bacteria from which to select DNA encoding G6PDH are *Leuconostoc* and *Zymomonas*. For example, *L. mesenteroides, L. citreum, L. lactis, L. dextranicum,* and *Z. mobilis*. In some embodiments, the bacteria are selected from, *L. mesenteroides, L. citreum,* and *L. lactis*. In some embodiments, G6PDH from *Leuconostoc* is used for mutation strategies wherein one or more cysteine residues are introduced as it does not contain cysteine residues.

Table 1 of U.S. Pat. No. 6,033,890, the disclosure of which is incorporated by reference in its entirety, describes exemplary strains of various *Leuconostoc* species. In some embodiments, strains from which to select G6PDH are *Leuconostoc mesenteroides* strain ATCC 12291, *Leuconostoc* citreum strain NCIMB 3351, *Leuconostoc lactis* strain NCDO 546, and *Leuconostoc* dextranicum strain ATCC 19255. In some embodiments, other G6PDH suitable for use in the present disclosure include, but are not limited to, those described in *Bacillus megaterium* M1286 (Heilman et al., Eur. J. Biochem. (1988) vol. 174, 485-490); *Saccharomyces cerevisiae* (Jeffrey et al., Biochemistry, (1985) vol. 24, 666-671); *Pichia jadinii* (Jeffrey et al., Biochem. Biopys. Res. Comm., (1989) vol. 160:3, 1290-1295), *E. coli* K-12 (Rowley et al., J. Bacterial., (1991) vol. 173:3, 968-977), and from human (Bhadbade et al., FEES Lett. (1987) vol. 211, 243-246).

In some embodiments, an enzyme from natural or recombinant sources or site-directed mutants, and any isoform, site-directed mutant or a mixture of isoforms and site-directed mutants may be used. For example, G6PDH from natural or recombinant sources or site-directed mutants, and any isoform, site-directed mutant or a mixture of isoforms and site-directed mutants may be used. Several G6PDH enzymes from various species are known as described herein, in U.S. Pat. No. 6,033,890 and by Levy (Adv. Enzym. (1979) vol. 48, 97-192). In some embodiments, an enzyme (e.g., G6PDH) from natural sources may be purified following procedures known to the skilled artisan.

In some embodiments, the enzyme is a recombinant enzyme. In some embodiments, the G6PDH is a recombinant G6PDH. The basic molecular biological techniques employed in generating a recombinant G6PDH can include methods such as DNA and plasmid isolation, restriction enzyme digestion, DNA ligation, purification and characterization of DNAs by polyacrylamide and agarose gel electrophoresis, labeling and hybridization of DNAs, Southern blotting, transformation, maintenance and growth of bacterial strains, protein expression and protein purification, and other general techniques are all well known in the art. For example, general techniques of molecular biology are described in "Molecular Cloning A Laboratory Manual" by Sambrook, J., Fritsch, E. F., and Maniatis, T. published by Cold Spring Harbor Laboratory Press, 2nd edition, 1989, or "A Practical Guide to Molecular Cloning" by Bernard Perbal published by John Wiley & Sons, New York, 1984. In some embodiments, the DNA encoding a G6PDH of interest is cloned into an expression vector and transformed into a suitable host cell, which expresses the recombinant G6PDH. In some embodiments, the recombinant G6PDH may then be purified using methods known to the skilled artisan. Recombinant G6PDH enzymes have been described and include, but are not limited to, G6PDHs from *L. mesenteroides* (Adams et al., J. Biol. Chem., (1983) vol. 258:9, 5867-5868; Murphy et al., J. Bacterial., (1987) vol. 169:1, 334-339; Lee et al., J. Biol. Chem., (1991) vol. 266:20, 13028-13034); *Z.* mobiles (Barnell et al., J. Bacterial., (1990) vol. 172:12, 7227-7240); *Bacillus megaterium* M1286 (Heilmann et al., Eur. J. Bio-chem., (1988) vol. 174, 485-490); and *E. coli* K-12 (Rowley et al. J. Bacterial., (1991) vol. 173:3, 968-977).

In some embodiments, the enzyme is a mutated enzyme. In some embodiments, the G6PDH is a mutated G6PDH. In some embodiments, G6PDHs differing from any naturally occurring G6PDH may be generated using molecular DNA cloning technologies as known in the art. In some embodiments, G6PDHs with amino acid substitutions, deletions, or insertions, or any combination thereof may be generated (see U.S. Pat. No. 6,033,890, which is incorporated by reference in its entirety) and used in the methods of this disclosure.

In some embodiments, the enzyme is obtained from a commercial source. In some embodiments, the Glucose-6-Phosphate Dehydrogenase (G6PDH) is obtained from a commercial source (e.g., Sigma, Biochemica, Boehringer Mannheim, USE Biochemical, and OYC International Inc., which is incorporated by reference in its entirety), and its activity is determined either experimentally or is provided by the manufacturer. In some embodiments, the starting activity of the G6PHD is greater than about 400 U/mg. For example, the starting activity of the G6PDH is greater than about 500 U/mg, greater than about 600 U/mg, greater than about 700 U/mg, greater than about 800 U/mg, greater than about 900 U/mg, greater than about 1,000 U/mg, greater than about 1,100 U/mg, or greater than about 1,200 U/mg. In some embodiments the starting activity of the G6PDH is greater than about 850 U/mg.

In some embodiments, the aqueous medium used in the methods provided herein further comprises an enzyme substrate for G6PDH and a coenzyme for G6PDH. In some embodiments, the method for determining the presence or absence of an analyte of interest in a keratinized structure (e.g., hair) sample further comprises detecting a change in the enzymatic activity of the enzyme-analyte conjugate, wherein the change in enzymatic activity is related to the amount of the analyte of interest present in the sample. In some embodiments, the enzymatic activities of G6PDH, the G6PDH-analyte conjugate, the G6PDH-analyte conjugate with bound antibody and the G6PDH-analyte conjugate with bound antibody competing for analyte binding in a test sample are determined. In some embodiments, determination of enzymatic activity is dependent on a substrate and co-enzyme for G6PDH. In some embodiments, a suitable substrate for G6PDH is glucose-6-phosphate (G6P). In some embodiments, suitable co-enzymes or cofactors for G6PDH are NAD (NAD+) and NADP (NADP+). In some embodiments, G6PDH converts G6P and co-enzymes into 6-P-glucuronate and NADH and NADPH, respectively. In some embodiments, in order to measure G6PDH activity, G6P and NAD+ or NADP+ are added to the aqueous medium. In some embodiments, cofactor analogs, such as thio-NAD+, thio-NADH, thio-NADP+, or thio-NADPH may also be used.

In some embodiments, substrate and co-enzyme or co-factors for G6PDH are not labeled and the signal generated by G6PDH, i.e., the amount of NADPH or NADH, is measured in a spectrophotometer as described herein. In some embodiments, the substrate and or co-enzymes may be labeled and the signal generated by G6PDH may be detected by other means, depending on the label, such as by measuring change in fluorescence or scintillation count, or the like.

Provided herein, is a method for determining the presence or absence of an analyte of interest in a keratinized structure (e.g., hair) sample comprising, combining in an aqueous medium an enzyme-analyte conjugate comprising glucose-6-phosphate dehydrogenase (G6PDH) covalently linked to the analyte of interest, an antibody specific for the analyte of interest, a keratinized structure (e.g., hair) sample, an enzyme substrate for G6PDH, and a coenzyme for G6PDH, and determining if the analyte of interest is present of absent in the keratinized structure (e.g., hair) sample using any suitable method including those described herein. In some embodiments, the keratinized structure sample is a hair sample. In some embodiments, the keratinized structure sample is a nail sample. For example, the nail sample can be a toenail sample or a fingernail sample.

Analytes

In some embodiments, the disclosure provides a conjugate comprising an enzyme and the analyte of interest. In some embodiments, an analyte of the disclosure can be any substance, compound or composition whose presence or concentration in a sample or specimen is to be determined.

In some embodiments, analytes can be polyepitopic or monoepitopic. In some embodiments, monoepitopic analytes will have a molecular weight from about 100 to 5,000 molecular weight, from about 500 to 3,000 molecular weight, or from about 125 to 2,000. In some embodiments, polyepitomic analytes will have a molecular weight of at least 5,000 molecular weight, at least about 7,500 molecular weight, or at least about 10,000 molecular weight. In some embodiments, poly amino acid analytes of interest may include proteins, polypeptides and peptides and can be from about 5,000 to 5,000,000 molecular weight, from about 10,000 to 2,500,000 molecular weight, or from about 20,000 to 1,000,000 molecular weight.

In some embodiments, the analyte of interest is selected from the group consisting of a drug of abuse, a toxic chemical, an environmental chemical, a petroleum product, a natural product, an organic compound, a nutrient, a prescription and over-the-counter medication, or a metabolite, derivative, or breakdown product of any of the foregoing. In some embodiments, the analyte of interest is a drug of abuse or metabolite thereof. In some embodiments, the drug of abuse or metabolite thereof is selected from the group consisting of cocaine, benzoylecgonine, cocaethylene, norocaine, phencyclidine (PCP), amphetamine, methamphetamines, cannabinoids, THC, carboxy-THC, heroin, codeine, morphine, 6-monoacetylmorphine (MAM), oxycodone, 3,4-methylenedioxyamphetamine (MDA), and 3,4-methylenedioxymethamphetamine (MDMA). In some embodiments, the analyte of interest is selected from the group consisting of opioids, amphetamines, NSAIDS, steroids, cannabinoids, benzodiazepines, barbiturates, tricyclics, and ephedrines, or metabolites, derivatives, or breakdown products of any of the foregoing.

In some embodiments, the analyte of interest is selected from the group consisting of cocaine, morphine, 6-Acetyl morphine (6-AM), hydrocodone, oxycodone, oxymorphone, methamphetamine, 3,4-methylenedioxymethamphetamine (MDMA), and phencyclidine (PCP).

Non-limiting examples of analytes of interest that may be used with the methods disclosed herein are licit and illicit drugs, sugars (including, but not limited to, mono-, di-, and poly-carbohydrates), amino acids, peptides, nucleic acids, nucleosides, nucleotides, vitamins, hormones, steroids, antibiotics, bacterial or microbial antigens, toxins, chemical and biological warfare agents, pesticides, herbicides, industrial chemicals and pollutants and include analogs, derivatives and metabolites of such compounds. Additional non-limiting examples of analytes of interest that may be used with the methods disclosed herein are opium, the opioid analgesics, alkaloids, catecholamines, epinephrine, amphetamines, barbiturates, benzodiazepines, cardiac drugs, anti-seizure drugs, immunosuppressants, tetrahydrocannabinol (THC, the active ingredient in marijuana), cocaine, cocaine metabolite (benzoylecgonine), crack, inhalants (e.g., amyl or butyl nitrates), phencyclidine (PCP), 3,4-methylendioxymethamphetamine (MDMA, or ecstasy) and its related compounds such as 3,4-methylendioxyamphetamine (MDA) and 3,4-methylenedioxyethylamphetamine (MDEA), ketamine, lysergic acid diethylamide (LSD), γ-hydroxybutyrate (GHB), methaqualone (also called quinazolinone), tranquilizers, alcohol, etc. In some embodiments, included in these classes are analogs, metabolites, and derivatives of such compounds. In some embodiments, the analyte of interest is an opioid analgesic. Non-limiting examples or opioid analgesics include opium, morphine, heroin, codeine, dihydrocodeine (DF-118), hydromorphone, fentanyl, oxycodone, buprenorphine, butorphanol, nalbuphine, methadone, physeptone, pethidine, dioconal, palium, dextromoramide, dipipanone, phenadoxone, propoxyphene (Darvon®), dextroproxyphene, pethidine, methylphenidate (Ritalin), acetylmethadol, and include analogs, metabolites, and derivatives of such opioid analgesics.

In some embodiments, the analyte of interest is an alkaloid. Non-limiting examples of alkaloids that may be used with the methods disclosed herein are steroid alkaloids, the iminazolyl alkaloids, the isoquinoline alkaloids, the quinoline alkaloids (including quinine), the diterpene alkaloids, and include analogs, metabolites, and derivatives of such alkaloids.

In some embodiments, the analyte of interest is a catecholamine. Non-limiting examples of catecholamines that may be used with the methods disclosed herein are cotamine, narceine, noscapine and papaverine epinephrine, L-dopa, ephedrine, and include analogs, metabolites, and derivatives of such catecholamines.

In some embodiments, the analyte of interest is an amphetamine or a related compound. Non-limiting examples of amphetamines and related compounds include amphetamine, methamphetamine, and the like. In some embodiments, included are analogs, metabolites, and derivatives of such amphetamines or related compounds.

In some embodiments, the analyte of interest is a barbiturate. Non-limiting examples of barbiturates include veronal, pentobarbital (Nembutal), amobarbital, secobarbital (Seconal), phenobarbital, thiopental, and include analogs, metabolites, and derivatives of such barbiturates. In some embodiments, the analyte of interest is a benzodiazepine. Non-limiting examples of benzodiazepines include Diazepam (Valium), chlordiazepoxide (Librium), Nitrazepam (Mogodon), Temazepam, and include analogs, metabolites, and derivatives of such benzodiazepines. In some embodiments, analyte is a hallucinogen. Non-limiting examples of hallucinogens include mescaline, psilocybin, psilocin, dextromoramide (Palfium), LSD, MDA (3,4-methylenedioxyamphetamine), Ecstacy (MDMA, 3,4-methylenedioxymethamptamine), MDEA (3,4-methylenedioxyethylamphetamine), PMA (para-methoxyamphetamine), PMMA (para-methoxymethylamphetamine), PCP (phencyclidine), and include analogs, metabolites, and derivatives of such hallucinogens.

In some embodiments, the analyte of interest is a cardiac drug. Non-limiting examples of cardiac drugs include digoxin, digitoxin, N-acetyl procainamide, procainamide, quinidine, lidocaine, and include analogs, metabolites, and derivatives of such cardiac drugs. In some embodiments, the analyte is an anti-seizure drug. Non-limiting examples of anti-seizure drugs include phenytoin, Phenobarbital, primidone, valproic acid, ethosuximide, carbamazepine, and include analogs, metabolites, and derivatives of such anti-seizure drugs. In some embodiments, the analyte is an immunosuppressant. Non-limiting examples of immunosuppressant include MPA (mycophenolic acid), cyclosporine, rapamycin (sirolimus), FK506 (tacrolimus), and include analogs, metabolites, and derivatives of such immunosuppressants.

Further non-limiting examples of an analyte of interest contemplated by the methods as provided herein include vitamins and diet supplements such as folic acid, thiamine, Vitamin B12, biotin, Vitamin A, Vitamin B, Vitamin C, Vitamin D, Vitamin E, Vitamin K, tranquilizers such as meprobamate, and tricyclic anti-depressants, food supplements and other performance-enhancing agents, and include analogs, metabolites, and derivatives of such compounds.

In some embodiments, the analyte of interest is an amino acid. Non-limiting examples of amino acids include glycine, alanine, serine, histidine, methionine, and include analogs, metabolites, and derivatives of such amino acids. In some embodiments, the analyte of interest is an antibiotic. Non-limiting examples of antibiotics include penicillin, chloromycetin, actinomycin, tetracycline, terramycin, gentamycin, kanamycin, tobromycin, tobramycin, netilmicin, amikacin, vancomycin, and include analogs, metabolites, and derivatives of such antibiotics. In some embodiments, the analyte of interest is a microbial antigen. Non-limiting examples of microbial antigens include *Clostridium difficile* antigen, Toxin A, aflatoxin B1, and include analogs, metabolites, and derivatives of such microbial antigens.

In some embodiments, the analyte of interest is a hormone. Non-limiting examples of hormones include thyroid hormones (T3 and T4), thyroxine, thyroid stimulating hormone, estrogen, progesterone, testosterone, prolactin, follicle stimulating hormone, chorionic gonadotropin, luteinizing hormone, include analogs, metabolites, and derivatives of such hormones. In some embodiments, the analyte is a steroid. Non-limiting examples of steroids include various estrogens and androgens such as ethynylestradiol, testosterone, androsterone, and include analogs, metabolites, and derivatives of such steroids.

In some embodiments, the analyte of interest is a chemical or biological warfare agent. Non-limiting examples of chemical or biological warfare agents include mustard gas, Sarin, Tabun, *Bacillus anthracis* (Anthrax) antigens, Smallpox viral antigens, and include analogs, metabolites, and derivatives of such chemical or biological warfare agents. In some embodiments, the analyte of interest is an industrial chemical. Non-limiting examples of industrial chemicals include flavoring agents, food additives, preservatives, food contaminants, air and chemical pollutants, pesticides, herbicides, and include analogs, metabolites, and derivatives of such industrial chemicals.

Provided herein is a method for determining the presence or absence of an analyte of interest in a keratinized structure (e.g., hair) sample comprising, combining in an aqueous medium an enzyme-analyte conjugate comprising glucose-6-phosphate dehydrogenase (G6PDH) covalently linked to the analyte of interest, an antibody specific to the analyte of interest, a keratinized structure (e.g., hair) sample, an enzyme substrate for G6PDH, and a coenzyme for G6PDH, and determining if the analyte of interest is present or absent in the keratinized structure (e.g., hair) sample, wherein the analyte of interest is a drug of abuse or metabolite thereof.

Conjugation

In some embodiments, the enzyme (e.g., G6PDH) is covalently linked to the analyte of interest. In some embodiments, the enzyme (e.g., G6PDH) is covalently linked to an analyte that is identical or substantially identical to the specific analyte of abuse to be measured. In some embodiments, the substantially identical analyte has greater than about 80% cross-reactivity to the analyte. For example, the substantially identical analyte has greater than about 85%, greater than about 90%, greater than about 95%, or greater than about 98% cross-reactivity to the analyte.

In some embodiments, conjugation can be achieved via conventional chemical reactions as known in the art. For example, a reaction to coupling an analyte (or a hapten) to the enzyme (e.g., G6PDH) is through the formation of a peptide bond (—$CONH_2$). Non-limiting examples include using a carboxyl (—COOH) group on an analyte (or a hapten) to react with an amino group (—$NH_2$) on the G6PDH enzyme (Biochem. and Biophys. Res. Comm., (1989) vol. 160:3, 1290-1295). Glucose-6-phosphate dehydrogenase from *Leuconostoc mesenteroides* is reported to contain a total of 38 lysine residues (Levy, Adv. Enzym, (1979) vol. 48, 97-192; FEBS Lett. 211:2, 243-246, 1987). In some embodiments, under appropriate coupling conditions, the €-amino groups from these lysine moieties can be modified readily. In some embodiments, multiple molecules of an analyte (or hapten) and/or a plurality of analytes (or haptens) can be conjugated to each molecule of the enzyme (e.g., G6PDH).

In some embodiments, analytes are capable of binding directly to the enzyme (e.g., G6PDH). In some embodiments, analytes are not capable of covalent binding directly. In some embodiments, analytes not capable of covalent binding directly are rendered capable of covalently binding to the enzyme (e.g., G6PDH) by the addition of a linking group that can covalently bind to a group on the enzyme (e.g., G6PDH) (e.g., to an amino, hydroxyl, carboxyl or mercapto group). Non-limiting examples of linking groups include amino acids having one or more free amino or free hydroxyl groups, carbonyl, thiocarbonyl, or carboxyl groups, or compounds containing such groups. Additional non-limiting examples of linking groups include N-hydroxysuccinimide and other succinimide or maleimide-containing moieties, and 1-(3-dimethylpropyl)-3-ethylcarbodiimide. Further non-limiting examples of linking groups are found in U.S. Pat. No. 3,817,837, which is incorporated by reference in its entirety.

In some embodiments, linking groups suitable for use in this disclosure include compounds of about less than 50 atoms other than hydrogens, about less than 20 atoms other than hydrogens, about less than 6 atoms other than hydrogens and having a chain (i.e., a spacer) of not more than about 35, less than about 15, less than about 10, or less than about 5 atoms in length. Non-limiting examples of linking groups usable in preparing conjugates for this disclosure include bifunctional crosslinking or coupling agents (i.e., molecules containing two reactive groups or "ends"), which may be tethered by a spacer of variable length. In some embodiments, the reactive ends can be any of a variety of functionalities including, but not limited to, amino reacting ends such as N-hydroxysuccinimide (NHS) active esters, imidoesters, aldehydes, epoxides, sulfonyl halides, isocyanate, isothiocyanate, and nitroaryl halides; and thiol reacting ends such as pyridyl disulfides, maleimides, and thiophthalimides. In some embodiments, the heterobifunctional cross-linking reagents have two different reactive ends (e.g., an amino-reactive end and a thiol-reactive end) while homobifunctional reagents that are usable in preparing the conjugates of this disclosure have two similar reactive ends. Non-limiting examples of such include bismaleimidohexane (BMH), which permits the cross-linking of sulfhydryl-containing compounds, and NHS homobifunctional crosslinkers such as disuccinimidyl suberate (DSS) as well as the water soluble analogs, sulfo-NHS esters. Additional non-limiting examples of suitable linking groups for use in the present disclosure include maleimido-NHS active esters coupling agents such as m-maleimidobenzoyl-N-hydroxy-succinimide ester (MBS); succinimidyl 4-(N-maleimidomethyl)cyclohexane-1-carboxylate (SMCC); succinimidyl 4-(p-maleimidophenyl)butyrate (SMPB) and derivatives thereof, including sulfosuccinimidyl derivatives such as sulfosuccinimidyl 4-(N-maleimido-methyl) cyclohexane-1-carboxylate (sulfo-SMCC); m-maleimidobenzoyl-sulfosuccinimide ester (sulfo-MBS) and sulfosuccinimidyl 4-(p-maleimidophenyl)butyrate (sulfo-SMPB) (Pierce). Non-limiting examples of suitable heterobifunctional reagents include commercially available active halogen-NETS active esters coupling agents such as N-succinimidyl bromoacetate and N-succinimidyl (4-iodoacetyl)aminobenzoate (SIAB) and the sulfo-succinimidyl derivatives such as sulfosuccinimidyl (4-iodoacetyl)aminobenzoate (sulfo-SIAB) (Pierce). Another non-limiting example of coupling agents is the heterobifunctional and thiol cleavable agents such as N-succinimidyl 3-(2-pyridyidithio-)propionate (SPDP) (Pierce).

Non-limiting examples of commercially available homobifunctional cross-linking reagents include the imidoesters such as dimethyl adipimidate dihydrochloride (DMA); dimethyl pimelimidate dihydrochloride (DMP); and dimethyl suberimidate dihydrochloride (DMS).

In some embodiments, the conjugates are prepared by contacting the activated analyte or hapten with a buffered solution of enzyme (e.g., G6PDH) under conditions for formation of such conjugates. In some embodiments, conditions for forming such conjugates include a temperature of from about 2° C. to about 25° C., a pH of from about 5 to about 10, and a contact time of from less than an hour to several days.

In some embodiments, the enzyme-analyte conjugate is purified after conjugation. For example, suitable purification procedures are known in the art and non-limiting examples include dialysis against aqueous/organic and aqueous solutions such as water/DMF or water, or by gel filtration chromatography on supports such as Sephadex, and the like.

Deactivation of G6PDH

In some embodiments, covalently linking an analyte of interest to the enzyme (e.g., G6PDH) leads to a change of enzymatic activity (e.g., G6PDH enzymatic activity), which can be measured using the methods of this disclosure. In some embodiments, this change of enzymatic activity is a decrease of enzymatic activity by the enzyme-analyte conjugate (e.g., G6PDH-analyte conjugate) when compared to the activity of the native enzyme (e.g., G6PDH), i.e., the enzyme (e.g., G6PDH), which is not conjugated to an analyte. In some embodiments, the decrease of enzymatic activity due to the covalent linking of an analyte to the enzyme (e.g., G6PDH) is referred to as deactivation. In some embodiments, covalent linkage of the analyte to the enzyme (e.g., G6PDH) results in permanent deactivation of the enzyme.

In some embodiments, the ratio of analyte conjugated to the enzyme (e.g., G6PDH) is dependent on the desirable % of deactivation of the enzyme (e.g., G6PDH) and the desirable % inhibition of the resulting enzyme-analyte conjugate (e.g., G6PDH-analyte conjugate) exhibited upon binding to the specific antibody. In some embodiments, the extent of deactivation will be proportional to the extent of conjugation. In some embodiments, the extent of deactivation may be controlled, for example, by measuring enzymatic activity on samples taken at various times of conjugation.

In some embodiments, the inhibition of the enzyme-analyte conjugate (e.g., G6PDH-analyte conjugate) is from about 20% to about 50%. In some embodiments, the enzyme (e.g., G6PDH) is deactivated by from about 20% to about 60% and the enzyme activity of the deactivated enzyme-analyte conjugate (e.g., G6PDH-analyte conjugate) is further inhibited by from about 40% to about 80%. In some embodiments, the enzyme (e.g., G6PDH) is deactivated by from about 30% to about 65% and the enzyme activity of the deactivated enzyme-analyte conjugate (e.g., G6PDH-analyte conjugate) is further inhibited by from about 40% to about 85%.

In some embodiments, the higher the specific activity of the enzyme-analyte conjugate (e.g., G6PDH-analyte conjugate), the higher the assay sensitivity. In some embodiments, the enzyme-analyte conjugate (e.g., G6PDH-analyte conjugate) has a minimum specific activity. In some embodiments, with about 10% deactivation, the specific activity of the enzyme-analyte conjugate (e.g., G6PDH-analyte conjugate) is in the range of about 450 U/mg to about 1,800 U/mg, in the range of about 540 U/mg to about 1,350 U/mg, or in the range of about 630 units/mg to about 900 units/mg. In some embodiments, enzyme-analyte conjugate (e.g., G6PDH-analyte conjugate) has a specific activity of at least about 720 U/mg. In some embodiments, the enzyme-analyte conjugate (e.g., G6PDH-analyte conjugate) has a specific activity of at least about 810 U/mg.

In some embodiments, with about 20% deactivation, the specific activity of the enzyme-analyte conjugate (e.g., G6PDH-analyte conjugate) is in the range of about 400 U/mg to about 1,600 U/mg, in the range of about 480 U/mg to about 1,200 U/mg, or in the range of about 560 U/mg to about 800 U/mg. In some embodiments, the enzyme-analyte conjugate (e.g., G6PDH-analyte conjugate) has a specific activity of at least about 640 U/mg. In some embodiments, the enzyme-analyte conjugate (e.g., G6PDH-analyte conjugate) has a specific activity of at least about 720 U/mg.

In some embodiments, with about 30% deactivation, the specific activity of the enzyme-analyte conjugate (e.g., G6PDH-analyte conjugate) is in the range of about 350 U/mg to about 1,400 U/mg, in the range of about 420 U/mg to about 1,050 U/mg, or in the range of about 490 U/mg to about 700 U/mg. In some embodiments, the enzyme-analyte conjugate (e.g., G6PDH-analyte conjugate) has a specific activity of at least about 560 U/mg. In some embodiments, the enzyme-analyte conjugate (e.g., G6PDH-analyte conjugate) has a specific activity of at least about 630 U/mg.

In some embodiments, with about 40% deactivation, the specific activity of the enzyme-analyte conjugate (e.g., G6PDH-analyte conjugate) is in the range of about 30 U/mg to about 1,200 U/mg, in the range of about 360 U/mg to about 900 U/mg, or in the range of about 420 U/mg to about 600 U/mg. In some embodiments, the enzyme-analyte conjugate (e.g., G6PDH-analyte conjugate) has a specific activity of at least about 480 U/mg. In some embodiments, the enzyme-analyte conjugate (e.g., G6PDH-analyte conjugate) has a specific activity of at least about 540 U/mg.

In some embodiments, with about 50% deactivation, the specific activity of the enzyme-analyte conjugate (e.g., G6PDH-analyte conjugate) is in the range of about 250 U/mg to about 1,000 U/mg, in the range of about 300 U/mg to about 750 U/mg, or in the range of about 350 U/mg to about 500 U/mg. In some embodiments, the enzyme-analyte conjugate (e.g., G6PDH-analyte conjugate) has a specific activity of at least about 400 U/mg. In some embodiments, the enzyme-analyte conjugate (e.g., G6PDH-analyte conjugate) has a specific activity of at least about 450 U/mg.

In some embodiments, with about 60% deactivation, the specific activity of the enzyme-analyte conjugate (e.g., G6PDH-analyte conjugate) is in the range of about 200 U/mg to about 800 U/mg, in the range of about 240 U/mg to about 600 U/mg, or in the range of about 280 U/mg to about 400 U/mg. In some embodiments, the enzyme-analyte conjugate (e.g., G6PDH-analyte conjugate) has a specific activity of at least about 320 U/mg. In some embodiments, the enzyme-analyte conjugate (e.g., G6PDH-analyte conjugate) has a specific activity of at least about 360 U/mg.

Antibodies

In some embodiments, antibodies used in this disclosure include one or more polypeptides substantially encoded by immunoglobulin genes or fragments of immunoglobulin genes. Non-limiting examples of immunoglobulin genes include the kappa, lambda, alpha, gamma, delta, epsilon and mu constant region genes, as well as myriad immunoglobulin variable region genes. In some embodiments, immunoglobulin light chains are classified as either kappa or lambda. In some embodiments, immunoglobulin heavy chains are classified as gamma, mu, alpha, delta, or epsilon, which define immunoglobulin classes, IgG, IgM, IgA, IgD and IgE, respectively.

In some embodiments, a typical immunoglobulin (antibody) structural unit is known to comprise a tetramer. In some embodiments, each tetramer is composed of two identical pairs of polypeptide chains, each pair having one "light" (about 25 kD) and one "heavy" chain (about 50-70 kD). In some embodiments, the N-terminus of each chain defines a variable region of about 100 to 110 or more amino acids primarily responsible for antigen recognition. In some embodiments, the terms variable light chain ($V_L$) and variable heavy chain ($V_H$) refer to these light and heavy chains respectively.

In some embodiments, antibodies may exist as intact immunoglobulins or as a number of well-characterized fragments produced by digestion with various peptidases. For example, pepsin digests an antibody below the disulfide linkages in the hinge region to produce $F(ab)_2$, a dimer of Fab, which itself is a light chain joined to $V_H$-$C_{H1}$ by a disulfide bond. In some embodiments, the $F(ab)_2$ may be reduced under mild conditions to break the disulfide linkage in the hinge region thereby converting the $(Fab)_2$ dimer into a Fab monomer. In some embodiments, the Fab monomer is essentially a Fab with part of the hinge region (see, Fundamental Immunology, W. E. Paul, ed., Raven Press, N.Y. (1993), for a more detailed description of other antibody fragments). In some embodiments, various antibody fragments are defined in terms of the digestion of an intact antibody, one of skill will appreciate that such Fab fragments may be synthesized de nova either chemically or by utilizing recombinant DNA methodology.

In some embodiments, the term antibody, also includes antibody fragments either produced by the modification of whole antibodies or synthesized de nova using recombinant DNA methodologies. Non-limiting examples of antibodies include single chain antibodies (antibodies that exist as a single polypeptide chain), single chain Fv antibodies (sFv or scFv) in which a variable heavy and a variable light chain are joined together (directly or through a peptide linker) to form a continuous polypeptide. In some embodiments, the single chain Fv antibody is a covalently linked $V_H$-$V_L$ heterodimer, which may be expressed from a nucleic acid including $V_H$- and $V_L$-encoding sequences either joined directly or joined by a peptide-encoding linker (Huston, et al. (1988) Proc. Natl. Acad. Sci. USA, 85: 5879-5883). In some embodiments, while the $V_H$ and $V_L$ are connected to each as a single polypeptide chain, the $V_H$ and $V_L$ domains associate non-covalently. In some embodiments, functional antibody molecules can be expressed on the surface of filamentous phage were single-chain Fv's (scFv), however, alternative expression strategies have also been successful. For example, Fab molecules can be displayed on phage if one of the chains (heavy or light) is fused to g3 capsid protein and the complementary chain exported to the periplasm as a soluble molecule. In some embodiments, the two chains can be encoded on the same or on different replicons; as long as the two antibody chains in each Fab molecule assemble post-translationally and the dimer incorporated into the phage particle via linkage of one of the chains to g3p (see, e.g., U.S. Pat. No. 5,733,743). In some embodiments, the scFv antibodies and a number of other structures converting the naturally aggregated, but chemically separated light and heavy polypeptide chains from an antibody V region into a molecule that folds into a three dimensional structure substantially similar to the structure of an antigen-binding site are known to those of skill in the art (see e.g., U.S. Pat. Nos. 5,091,513, 5,132,405, and 4,956,778).

In some embodiments, antibodies include all those that have been displayed on phage (e.g., scFv, Fv, Fab and disulfide linked Fv (Reiter et al. Protein Eng., (1995) vol. 8, 1323-1331). In some embodiments, antibodies can also include diantibodies, miniantibodies, humanized antibodies, or chimeric antibodies.

In some embodiments, the antibody specific for the analyte of interest is specific for an analyte selected from the group consisting of cocaine, benzoylecgonine, cocaethylene, norcocaine, PCP, amphetamine, methamphetamine, cannabinoids, THC, carboxy-THC, heroin, codeine, morphine, 6-monoacetylmorphine (MAM), oxycodone, 3,4-methylenedioxyamphetamine (MDA), and 3,4-methylenedioxymethamphetamine (MDMA). In some embodiments, the antibody is detectably labeled. In some embodiments, the antibody is detectably labeled with a fluorescent label, a luminescent label, a radioactive label, or an enzymatic label. In some embodiments, the luminescent label is a chemiluminescent label or a bioluminescent label.

Homogeneous Enzyme Immunoassay (HEIA)

In some embodiments, the method for determining the presence or absence of an analyte of interest further comprises detecting a change in the enzymatic activity of the enzyme-analyte conjugate, wherein the change in enzymatic activity is related to the amount of the analyte present in the sample. In some embodiments, the enzyme (e.g., G6PDH) can be further inhibited by binding of an analyte-specific antibody to the enzyme-analyte conjugate (e.g., G6PDH-analyte conjugate). In some embodiments, this inhibition is reversible; addition of a sample containing the analyte of interest to the antibody-enzyme conjugate (e.g., antibody-G6PDH conjugate) will result in release of the antibody from the enzyme (e.g., G6PDH) conjugate, thus restoring enzyme activity. In some embodiments, measurement of the increase in enzyme (e.g., G6PDH) activity upon addition of the sample containing the analyte of interest is proportional to the concentration of the analyte in the sample. In some embodiments, the assay is based on competition between the enzyme-analyte conjugate (e.g., G6PDH-analyte conjugate) and the free analyte of interest in the sample for a fixed amount of antibody binding sites.

In some embodiments, in the absence of analyte(s) in the sample, the antibody remains bound to the enzyme-analyte conjugate (e.g., G6PDH-analyte conjugate), with no change in enzyme activity. In some embodiments, when the analyte of interest is present in the sample, the antibody binds to analyte and the enzymatic activity of the enzyme-analyte conjugate (e.g., G6PDH-analyte conjugate) is increased in proportion to the concentration of analyte in the sample. In some embodiments, activity of the enzyme-analyte conjugate (e.g., G6PDH-analyte conjugate) is monitored by measuring the reduction of NAD or NADP to NADH or NADPH, respectively, at 340 nm. In some embodiments, measuring the signal produced by reduction of NAD to NADH by the enzyme-analyte conjugate (e.g., G6PDH-analyte conjugate) can be applied to automated clinical analyzers. For example, such automated clinical analyzers include, but are not limited to, the Roche Cobas series analyzers and Beckman Coulter AU series analyzers. In some embodiments, analyzers capable of maintaining constant temperature in the reaction chamber, pipetting 5 to 75 μL of sample, mixing reagents, measuring enzyme rates at 340 nm and timing the reaction accurately can be used to perform the method of the disclosure.

In some embodiments, the inhibition of the enzyme-analyte conjugate (e.g., G6PDH-analyte conjugate) used in the HEIA methods as provided herein is from about 20% to about 50%. In some embodiments, the inhibition of the enzyme-analyte conjugate (e.g., G6PDH-analyte conjugate) used in the HEIA methods as provided herein is from about 30% to about 40%. In some embodiments, the inhibition of the enzyme-analyte conjugate (e.g., G6PDH-analyte conjugate) used in the HEIA methods as provided here is about 40%.

In some embodiments, the solvent for the homogeneous assay is an aqueous medium containing less than about 20% of other polar solvents including, but not limited to, N,N-Dimethylformamide (DMF), acetonitrile, dimethylsulfoxide (DMSO) or methanol.

In some embodiments, the pH for the assay is between about 4.0 and about 11.0. In some embodiments, the pH for the assay is between about 5.0 and about 10.0, about 6.0 and about 9.0, or about 6.5 and about 8.5. In some embodiments, the pH for the assay is about 7.0 pH.

In some embodiments, the acceptable temperature for the assay is between about 4° C. to about 45° C. In some embodiments, the acceptable temperature for the assay is between about 30° C. to about 40° C. In some embodiments, the acceptable temperature for the assay is about 37° C.

In some embodiments, the order of addition of reagents in the assay is not critical. In some embodiments, the hair extract is combined with a reagent solution (referred to as Antibody Buffer, see Table 2) consisting of antibody, substrate and cofactor for the enzyme (e.g., G6PDH), followed by incubation. In some embodiments, the enzyme-analyte conjugate (e.g., G6PDH-analyte conjugate) is then added, and measurement of the enzyme-analyte conjugate (e.g., G6PDH-analyte conjugate) activity is performed.

In some embodiments, the duration of the incubation period is empirically determined. In some embodiments, the incubation period is about 30 seconds to about 5 minutes. In some embodiments, the incubation period is about 2 minutes to about 4 minutes. In some embodiments, the incubation period is about 3.6 minutes.

In some embodiments, in order to accurately measure the analyte concentration in a hair extract, the signal (expressed as $\Delta mA$, or change in milliabsorbance) generated between a negative calibrator, typically a calibrator with 0 ng of analyte per 10 mg hair and a cutoff calibrator, such as a calibrator with 2 ng analyte/10 mg hair by enzyme-analyte conjugate (e.g., G6PDH-analyte conjugate) should be at about 40-100 $\Delta mA$ (fixed mode). In some embodiments, the enzyme-analyte conjugate (e.g., G6PDH-analyte conjugate) generates about 40-100 $\Delta mA$ (fixed mode). In some embodiments, equation 1 states the relationship between signal intensity, enzyme activity and reaction volume.

$$\text{Enzyme Activity} = \Delta AU \times Vt / \text{NADH} \times VR2 \qquad \text{Equation 1}$$

Where the $\Delta AU$ is the signal generated by the enzyme (e.g., G6PDH), Vt is the total reaction volume in milliliter (mL) including the sample, R1 (Antibody Buffer, Table 2) and R2 (Enzyme Buffer, Table 3) reagents, NADH is the extinction coefficient of NADH, corresponding to 6.22 and VR2 is the volume of R2 (Enzyme Buffer, Table 3) in milliliter.

In some embodiments, to meet the volume of automated analyzers, the volume should be less than about 250 µL per assay, including sample, R1 (Antibody Buffer, Table 2) and R2 (Enzyme Buffer, Table 3) volume. In some embodiments, 25 µL of sample, 75 µL of R1 (Antibody Buffer, Table 2) and 25 µL of R2 (Enzyme Buffer, Table 3) is added to generate the 40 $\Delta mA$ of signal, resulting in the required enzymatic activity being 0.032 U/mL. In some embodiments, the calculated enzyme activity of 0.032 U/mL is the effective enzyme amount required to generate 40 $\Delta mAU$ between the inhibited (negative/no analyte) and the reversibly inhibited (calibrator).

Kits for Determining Analyte in a Keratinized Structure (e.g., Hair) Sample Extract Provided herein are kits, comprising a conjugate comprising an enzyme and an analyte of interest and an antibody specific for the analyte of interest. In some embodiments, the kits provided are used for testing the presence and accurately determining the amount of analyte in a keratinized structure (e.g., hair) sample extract. In some embodiments, the kits of the disclosure may contain one or more of the following components: an enzyme-analyte conjugate comprising G6PDH covalently linked to an analyte of interest, an antibody reactive to the analyte, an enzyme substrate for G6PDH, a co-enzyme for G6PDH, a buffer, calibrators or quality controls, and an instruction manual on how to perform the HEIA. In some embodiments, the keratinized structure sample is a hair sample. In some embodiments, the keratinized structure sample is a nail sample. For example, the nail sample can be a toenail sample or a fingernail sample.

In some embodiments, the antibody specific for the analyte of interest is specific for a drug of abuse or a metabolite thereof.

In some embodiments, the analyte of interest is selected from the group consisting of a drug of abuse, a toxic chemical, an environmental chemical, a petroleum product, a natural product, an organic compound, a nutrient, a prescription and over-the-counter medication, or a metabolite, derivative, or breakdown product of any of the foregoing. In some embodiments, the analyte of interest is a drug of abuse or metabolite thereof. In some embodiments, the drug of abuse or metabolite thereof is selected from the group consisting of cocaine, benzoylecgonine, cocaethylene, norcocaine, PCP, amphetamine, methamphetamines, cannabinoids, THC, carboxy-THC, heroin, codeine, morphine, 6-monoacetylmorphine (MAM), oxycodone, 3,4-methylenedioxyamphetamine (MDA), and 3,4-methylenedioxymethamphetamine (MDMA). In some embodiments, the analyte of interest is selected from the group consisting of opioids, amphetamines, NSAIDS, steroids, cannabinoids, benzodiazepines, barbiturates, tricyclics, and ephedrines, or metabolites, derivatives, or breakdown products of any of the foregoing.

In some embodiments, the antibody specific for the analyte of interest is specific for an analyte selected from the group consisting of cocaine, benzoylecgonine, cocaethylene, norcocaine, PCP, amphetamine, methamphetamine, cannabinoids, THC, carboxy-THC, heroin, codeine, morphine, 6-monoacetylmorphine (MAM), oxycodone, 3,4-methylenedioxyamphetamine (MDA), and 3,4-methylenedioxymethamphetamine (MDMA).

In some embodiments, reagents and compositions useful in the methods of the disclosure are provided in a packaged combination. In some embodiments, the reagents or compositions may be in the same or in separate containers depending on cross-reactivity and/or stability of the reagents. In some embodiments, the reagents may be in lyophilized form. In some embodiments, when reagents are provided as lyophilized powders, dissolving agents are included so that upon dissolution, the resulting reagent solution will have the correct concentration.

EXAMPLES

The methods as provided herein are further described in the following examples, which do not limit the scope of the disclosure described in the claims.

Example 1: Calibrators and Assay Reagents

Table 1 provides the calibrators and controls for each analyte. The calibrators and controls are prepared by spiking the analyte into negative hair extract buffer (e.g., 10 mM phosphate buffer, 0.0075% Tween, pH 2.4). The calibrators, controls and analyte samples are then heated to about 80° C. for a period of about 3 hours.

TABLE 1

Calibrators and Controls

| Analyte | −50% Control (ng/10 mg) | Cutoff Calibrator (ng/10 mg) | +100% Control (ng/10 mg) |
|---|---|---|---|
| Cocaine | 2.5 | 5 | 10 |
| Morphine | 1 | 2 | 4 |
| PCP | 1.5 | 3 | 6 |
| Methamphetamine | 1.5 | 3 | 6 |
| Oxycodone | 1 | 2 | 4 |

Tables 2 and 3 provide the composition of Antibody Buffer and Enzyme Buffer, respectively, which were used in the provided examples.

TABLE 2

Antibody Buffer

| Component | Amount |
|---|---|
| Tris (pH 5.4) | 20 mM |
| G6P | 40 mM |
| NAD | 35 mM |
| NaCl | 0.5% |
| $NaN_3$ | 0.09% |
| BSA | 0.1% |

The antibody was formulated into Antibody Buffer at concentrations from 0.4 μg/mL to 1.0 μg/mL.

TABLE 3

Enzyme Buffer

| Component | Amount |
|---|---|
| Tris (pH 8.2) | 50 mM |
| NaCl | 0.9% |
| $NaN_3$ | 0.09% |
| BSA | 0.1% |

The G6PDH-analyte conjugate was formulated into Enzyme Buffer at concentrations from 0.4 μg/mL to 0.5 μg/mL. The G6PDH-analyte conjugate was formulated into Enzyme Buffer to yield a cutoff calibrator ΔmAU of 40 to 100 at 37° C. in a fixed mode setting on the chemistry autoanalyzer.

Example 2: Assay Protocol

Seventy-five microliters of antibody reagent (diluted in Antibody Buffer) was incubated with 25 μL to 30 μL of calibrator or sample, followed by addition of 25 μL of G6PDH-analyte conjugate (diluted in Enzyme Buffer) at 37° C. The reaction was incubated at 37° C., and the absorbance monitored at 340 nm. The reaction was monitored for a time period of 216 seconds.

The absorbance between the first measurement and second measurement was used to calculate the ΔmAU. The maximum rate of the enzyme was calculated by substituting Antibody Buffer containing G6P and NAD alone for the Antibody Buffer containing G6P, NAD and antibody.

Example 3: Preparation of G6PDH-Analyte Conjugate

Haptens (e.g., cocaine, morphine, methamphetamine, phencyclidine, oxycodone) were synthesized in-house using methods known to those skilled in the art. All haptens were prepared for coupling to G6PDH via formation of an activated ester using Sulfo-N-Hydroxysuccinimide and 1-(3-Dimethylpropyl)-3-Ethylcarbodiimide in anhydrous DMF.

G6PDH was purchased as a lyophilized powder and resuspended to a concentration of 1 mg/mL using 10 mM Tris buffer, pH 7.4.

The activated ester of the hapten was added to the solution of resuspended G6PDH at 4° C., followed by rotating overnight at the same temperature. After this time period, the G6PDH-antigen conjugate was transferred to a dialysis cassette and dialyzed against buffer B (Table 3) that does not contain BSA. The conjugation was typically carried out at a 5-fold molar excess of antigen to the number of lysine residues per mole of G6PDH.

Example 4: Preparation of G6PDH-Methamphetamine Conjugate

G6PDH with a starting activity of 870 U/mg was purchased from a commercial source. G6PDH (1 mg) was conjugated with methamphetamine antigen; after purification, 0.5 mg of G6PDH-methamphetamine was isolated. The G6PDH-methamphetamine conjugate was reversibly inhibited by an antibody reactive to methamphetamine. The G6PDH-methamphetamine conjugate was formulated at 0.5 μg/mL for the immunoassay. In a typical immunoassay, 25 μL of sample, 75 μL of methamphetamine antibody and 25 μL of G6PDH-methamphetamine conjugate were used.

Example 5: Preparation of G6PDH-Oxycodone Conjugate

G6PDH with a starting activity of 891 U/mg was purchased from a commercial source. G6PDH (1 mg) was conjugated with oxycodone antigen; after purification 0.65 mg of G6PDH-oxycodone was isolated. The G6PDH-oxycodone conjugate was reversibly inhibited by an antibody reactive to oxycodone. The G6PDH-oxycodone conjugate was formulated at 0.4 μg/mL for the immunoassay. In a typical immunoassay, 25 μL, of sample, 75 μL, of oxycodone antibody and 25 μL, of G6PDH-oxycodone were used.

Example 6: Calibration and Determination of Cocaine in Hair Extract by Homogeneous Enzyme Immunoassay The data depicted in Table 4 and FIG. 1 were obtained using the protocol described in Example 1 for detecting cocaine in a hair extract sample by homogeneous enzyme immunoassay using cocaine antibody, G6PDH-cocaine conjugate, and a hair extract calibrator and controls.

TABLE 4

| Cocaine Conc. (ng/10 mg hair) | ΔmAU |
|---|---|
| 0 | 0.525 |
| 1.25 | 24.5 |
| 2.5 | 47.2 |
| 5 | 87.2 |
| 10 | 141.4 |

Figure 2:
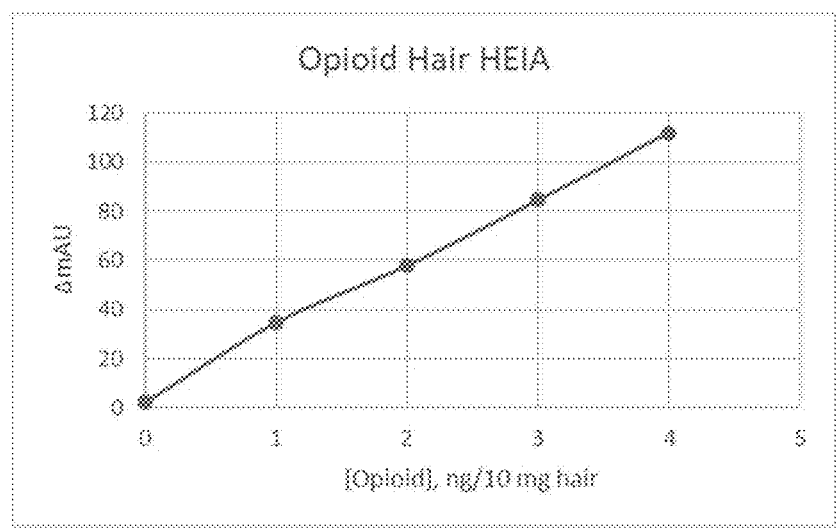
FIG. 2 is an exemplary graphical representation of a calibration curve for opioid obtained by plotting the results obtained in Example 7. The concentration of opioid is shown on the X-axis and the absorbance at 340 nm (ΔmAU) is shown on the Y-axis.

Example 7: Calibration and Determination of Opioids (e.g., Morphine, Codeine, 6-Acetylmorphine) in Hair Extract by Homogeneous Enzyme Immunoassay The data depicted in Table 5 and FIG. 2 were obtained using the protocol described in Example 1 for detecting opioids in a hair extract sample by homogeneous immunoassay using opioid antibody, G6PDH-opioid conjugate, and a hair extract with morphine calibrator and morphine controls. The assay had >80% cross reactivity with codeine and 6-acetylmorphine when using morphine as calibrator.

TABLE 5

| Opiod Conc. (ng/10 mg hair) | ΔmAU |
|---|---|
| 0 | 2.3 |
| 1.0 | 34.7 |

TABLE 5-continued

| Opiod Conc. (ng/10 mg hair) | ΔmAU |
|---|---|
| 2.0 | 57.9 |
| 4.0 | 111.9 |

Figure 3:
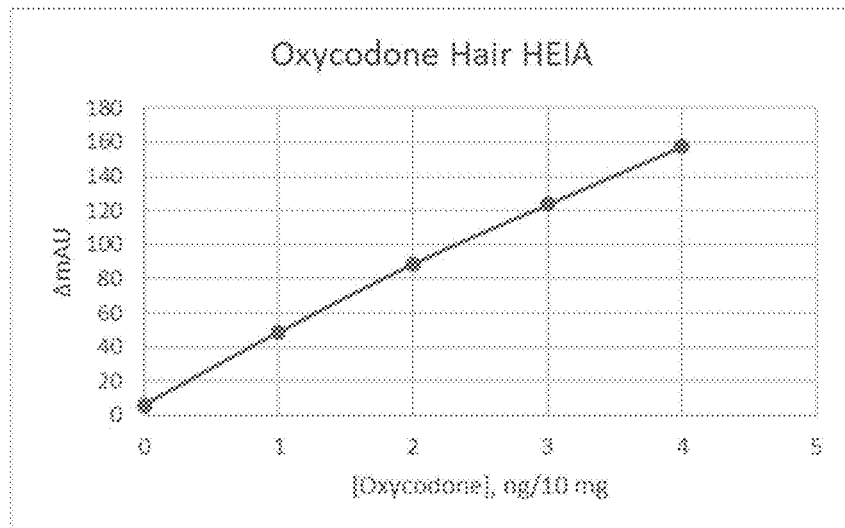
FIG. 3 is an exemplary graphical representation of a calibration curve for oxycodone obtained by plotting the results obtained in Example 8. The concentration of oxycodone is shown on the X-axis and the absorbance at 340 nm (ΔmAU) is shown on the Y-axis.

Example 8: Calibration and Determination of Oxycodone/Hydrocodone in Hair Extract by Homogeneous Enzyme Immunoassay The data depicted in Table 6 and FIG. 3 were obtained using the protocol described in Example 1 for detecting oxycodone/hydrocodone in a hair extract sample by homogeneous immunoassay using oxycodone antibody, G6PDH-oxycodone conjugate, and a hair extract with oxycodone calibrator and oxycodone controls. The assay had >80% cross reactivity with hydrocodone when using oxycodone as calibrator.

TABLE 6

| Oxycodone Conc. (ng/10 mg hair) | ΔmAU |
|---|---|
| 0 | 6.2 |
| 1 | 48.7 |
| 2 | 88.7 |
| 3 | 123.5 |
| 4 | 157.5 |

Figure 4:
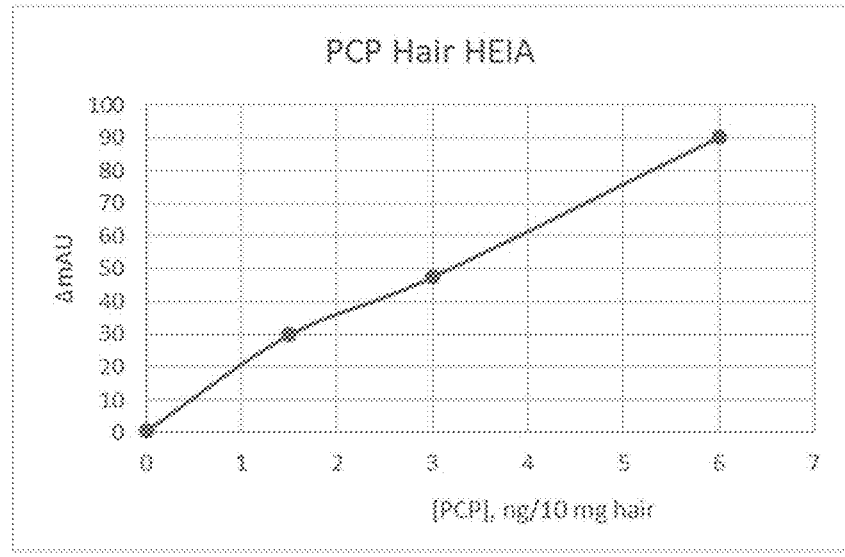
FIG. 4 is an exemplary graphical representation of a calibration curve for PCP obtained by plotting the results obtained in Example 9. The concentration of PCP is shown on the X-axis and the absorbance at 340 nm (ΔmAU) is shown on the Y-axis.

Example 9: Calibration and Determination of PCP in Hair Extract by Homogeneous Enzyme Immunoassay The data depicted in Table 7 and FIG. 4 were obtained using the protocol described in Example 1 for detecting PCP in a hair extract sample by homogeneous immunoassay using PCP antibody, G6PDH-PCP conjugate, and a hair extract with PCP calibrator and PCP controls.

TABLE 7

| PCP Conc. (ng/10 mg hair) | ΔmAU |
|---|---|
| 0 | 0.4 |
| 1.5 | 29.8 |
| 3 | 47.6 |
| 6 | 90.3 |

Figure 5:
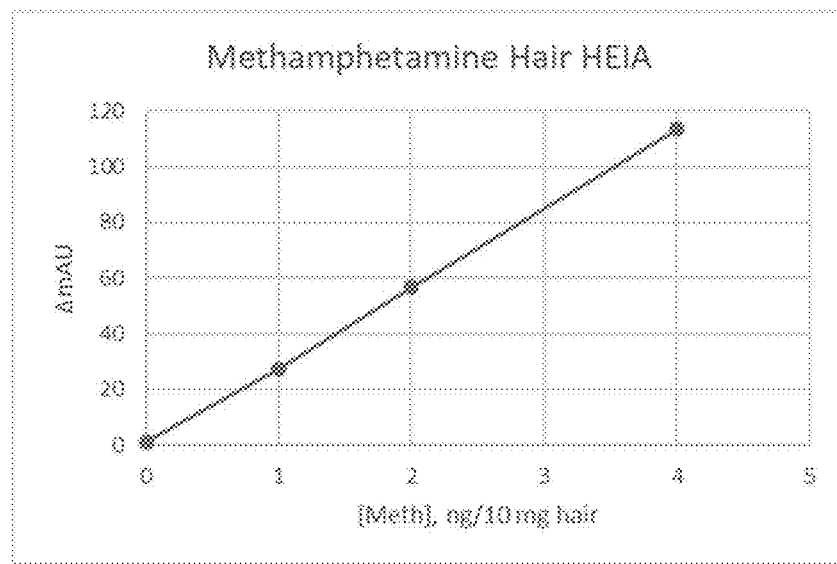
FIG. 5 is an exemplary graphical representation of a calibration curve for methamphetamine obtained by plotting the results obtained in Example 10. The concentration of methamphetamine is shown on the X-axis and the absorbance at 340 nm (ΔmAU) is shown on the Y-axis.

Example 10: Calibration and Determination of Methamphetamine in Hair Extract by Homogeneous Enzyme Immunoassay The data depicted in Table 8 and FIG. 5 were obtained using the protocol described in Example 1 for detecting methamphetamine in a hair extract sample by homogeneous immunoassay using methamphetamine antibody, G6PDH-methamphetamine conjugate, and a hair extract with methamphetamine calibrator and methamphetamine controls.

TABLE 8

| Methamphetamine Conc. (ng/10 mg hair) | ΔmAU |
|---|---|
| 0 | 1.02 |
| 1 | 27.4 |
| 2 | 56.7 |
| 4 | 113.6 |

OTHER EMBODIMENTS

It is to be understood that while the disclosure has been described in conjunction with the detailed description thereof, the foregoing description is intended to illustrate and not limit the scope of the disclosure, which is defined by the scope of the appended claims. Other aspects, advantages, and modifications are within the scope of the following claims.

What is claimed is:

1. A method of determining an amount of an analyte of interest in a keratinized structure sample at a sensitivity of between 2 ng and 5 ng analyte per about 10 mg sample, comprising:
   (a) combining in an aqueous medium:
       (i) a conjugate comprising an enzyme and the analyte of interest;
       (ii) an antibody specific for the analyte of interest; and
       (iii) the keratinized structure sample; and
   (b) determining the amount of the analyte of interest in the keratinized structure sample at a sensitivity of between 2 ng and 5 ng analyte per about 10 mg sample.

2. The method of claim 1, wherein the enzyme is selected from the group consisting of glucose-6-phosphate dehydrogenase (G6PDH), alcohol dehydrogenase, glutamic dehydrogenase, malic dehydrogenase, isocitric dehydrogenase, α-glycerol phosphate dehydrogenase, lactic dehydrogenase, glyceraldehydes-3-phosphate dehydrogenase, gluthathione reductase, quinine reductase, nitrate reductase, and glutamic dehydrogenase.

3. The method of claim 1, wherein the enzyme is glucose-6-phosphate dehydrogenase (G6PDH).

4. The method of claim 3, wherein the G6PDH is covalently linked to the analyte of interest.

5. The method of claim 1, wherein the analyte of interest is selected from the group consisting of cocaine, benzoylecgonine, cocaethylene, norcocaine, phencyclidine (PCP), amphetamine, methamphetamine, cannabinoids, tetrahydrocannabinol (THC), carboxy-THC, heroin, benzodiazepines, methadone, codeine, morphine, 6-monoacetylmorphine (MAM), oxycodone, 3,4-methylenedioxyamphetamine (MDA), and 3,4-methylenedioxymethamphetamine (MDMA).

6. The method of claim 1, wherein the antibody is detectably labeled.

7. The method of claim 3, wherein the aqueous medium further comprises:
   (a) an enzyme substrate for G6PDH; and
   (b) a coenzyme for G6PDH.

8. The method of claim 7, further comprising:
   detecting a change in the enzymatic activity of the enzyme-analyte conjugate, wherein the change in enzymatic activity is related to the amount of the analyte of interest present in the sample.

9. The method of claim 1, wherein the antibody is present at a concentration from 0.4 µg/mL to 1.0 µg/mL.

10. The method of claim 1, wherein the conjugate comprising an enzyme and the analyte of interest is present at a concentration from 0.4 μg/mL to 0.5 μg/mL.

11. The method of claim 1, wherein the amount of the analyte of interest is determined at a temperature of 30° C. to 40° C.

12. The method of claim 1, wherein the aqueous medium has a pH between 5.0 and 10.0.

13. The method of claim 1, wherein the aqueous medium contains less than 20% of N,N-dimethylformamide (DMF), acetonitrile, dimethylsulfoxide (DMSO), methanol, or a combination thereof.

14. The method of claim 1, wherein the analyte of interest is selected from the group consisting of cocaine, benzoylecgonine, cocaethylene, norocaine, phencyclidine (PCP), amphetamine, methamphetamines, cannabinoids, tetrahydrocannabinol (THC), carboxy-THC, nicotine, cotinine, benzodiazepines, heroin, codeine, morphine, 6-monoacetylmorphine (MAM), oxycodone, 3,4-methylenedioxyamphetamine (MDA), and 3,4-methylenedioxymethamphetamine (MDMA).

15. A method of determining an amount of an analyte of interest in a keratinized structure sample at a sensitivity of between 2 ng and 5 ng analyte per about 10 mg sample, comprising:

(a) combining in an aqueous medium:
  (i) an enzyme-analyte conjugate comprising glucose-6-phosphate dehydrogenase (G6PDH) covalently linked to the analyte of interest;
  (ii) an antibody specific for the analyte of interest;
  (iii) a keratinized structure sample;
  (iv) an enzyme substrate for G6PDH; and
  (v) a coenzyme for G6PDH; and
(b) determining the amount of the analyte of interest in the keratinized structure sample at a sensitivity of between 2 ng and 5 ng analyte per about 10 mg sample.

16. The method of claim 1, wherein the keratinized structure sample is a hair sample.

17. The method of claim 1, wherein the keratinized structure sample is a nail sample.

18. The method of claim 1, wherein step (a) further comprises extracting the analyte of interest from the keratinized structure using a buffer.

19. The method of claim 18, wherein the buffer is a phosphate buffer.

20. The method of claim 15, wherein step (a) further comprises extracting the analyte of interest from the keratinized structure using a buffer.

* * * * *